(12) United States Patent
Goettel et al.

(10) Patent No.: US 6,461,390 B1
(45) Date of Patent: Oct. 8, 2002

(54) PROCESS FOR MAKING 2-AMINOMETHYL-1, 4-DIAMINOBENZENE AND ITS SALTS AND COMPOSITIONS AND METHODS FOR DYEING KERATIN FIBERS USING SAME

(75) Inventors: Otto Goettel, Marly; Aline Pirrello, Givisiez; André Hayoz, Senèdes, all of (CH)

(73) Assignee: Wella Aktiengesellschaft, Darmstadt (DE)

( * ) Notice: Subject to any disclaimer, the term of this patent is extended or adjusted under 35 U.S.C. 154(b) by 105 days.

(21) Appl. No.: 09/668,330

(22) Filed: Sep. 22, 2000

(30) Foreign Application Priority Data

Dec. 18, 1999 (DE) .......................................... 199 61 229

(51) Int. Cl.$^7$ ................................................. A61K 7/13
(52) U.S. Cl. ........................ 8/405; 8/405; 8/406; 8/410; 8/416
(58) Field of Search ........................... 8/405, 406, 410, 8/416

(56) References Cited

U.S. PATENT DOCUMENTS 5,919,273 A * 7/1999 Rondeau et al. ............... 8/412

FOREIGN PATENT DOCUMENTS

| WO | 98/01106 | | 1/1998 | |
| WO | WO 98/01106 | * | 1/1998 | ............ A61K/7/13 |

OTHER PUBLICATIONS

Liebigs Annalen Der Chemie 1978, pp. 398–404.
Analogue Zu W. R. Baker, J. Org. Chem. 1983, 48, 5140.
"Heterocyclen Aus Diaminen Und Diacylverbindungen" By Hans–Joachim Kabbe, Justus Liebigs Annalen Der Chemie, Verlag 1978, pp. 398–404.

"A–amidoalkylation At Carbon . . . " By Harold E. Zaugg, Synthesis 1984, pp. 85–110.

\* cited by examiner

*Primary Examiner*—Yogendra N. Gupta
*Assistant Examiner*—Eisa B Elhilo
(74) *Attorney, Agent, or Firm*—Michael J. Striker

(57) ABSTRACT

A process is described for making 2-aminomethyl-1,4-diaminobenzene, or a physiologically compatible salt of 2-aminomethyl-1,4-diaminobenzene, of formula (I):

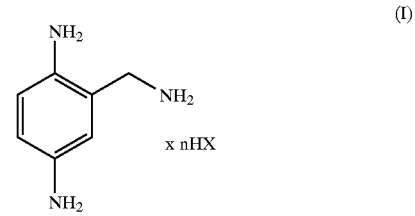

wherein n is a number from 0 to 3 and HX represents an inorganic or organic salt. In this process 2-(N-acylaminomethyl)-4-nitrophenol is first reacted with a halogen acetamide to form 2-(2-N-acylaminomethyl-4-nitrophenoxy)acetamide, which is then converted to 2-(N-acylaminomethyl)-4-nitroaniline. Subsequently the 2-(N-acylaminomethyl)4-nitroaniline is reduced to form 1,4-diamino-2-(N-acylaminomethyl)benzene, which is then deacylated by adding hydrochloric acid in a sufficient amount so that 1,4-diamino-2-aminomethylbenzene trihydrochloride is formed. Then the trichloride is converted to the free base form, 1,4-diamino-2-aminomethylbenzene, or to another salt of 1,4-diamino-2-amino-methylbenzene when n≠0 with the proviso that if n=3 HX is not hydrochloric acid. Compositions and methods for dyeing keratin fibers using the compounds of formula I are also described.

13 Claims, No Drawings

PROCESS FOR MAKING 2-AMINOMETHYL-1,4-DIAMINOBENZENE AND ITS SALTS AND COMPOSITIONS AND METHODS FOR DYEING KERATIN FIBERS USING SAME

BACKGROUND OF THE INVENTION

1. Field of the Invention

The subject matter of the present invention is a method for making 2-aminomethyl-1,4-diaminobenzene of formula (I) and its physiologically compatible salts with organic or inorganic salts. It also includes compositions and methods for dyeing keratin fibers containing the 2-aminomethyl-1,4-diaminobenzene or its physiologically compatible salts.

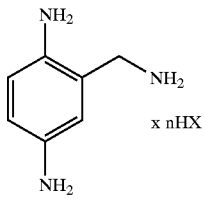

2. Prior Art 2-aminomethyl-1,4-diaminobenzene is known as a starting material for making certain heterocyclic compounds and is described in Liebigs Annals of Chemistry (Annalen der Chemie)1978, pp. 398–404. A method of making this compound is however not described. Also attempts to directly produce this compound from commercially obtained 2-amino-5-nitrobenzonitrile of formula (II) have been unsatisfactory in regard to reaction conditions, yield and product quality.

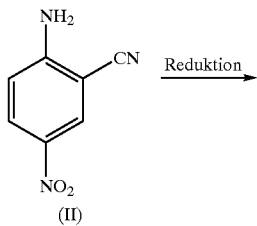

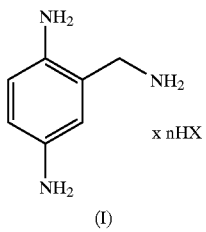

SUMMARY OF THE INVENTION

It is an object of the present invention to provide a simple manufacturing method for making 2-aminomethyl-1,4-diaminobenzene that provides easy production of its oxidation-insensitive salts.

It has now surprisingly been found that 2-aminomethyl-1,4-diamino-benzene may be obtained in a simple manner in good yield by aminomethylation of 4-nitrophenol, subsequent conversion to form the corresponding phenoxyacetamide, rearrangement to form the nitroaniline and finally reduction.

The subject matter of the present invention is thus a method for making. 2-aminomethyl-1,4-diaminobenzene or its physiologically compatible salts of formula (I):

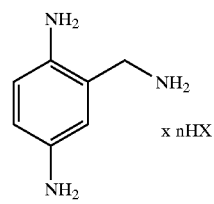

wherein n is a number from 0 to 3 and HX represents an inorganic or organic salt, which comprises a) reacting 2-(N-acylaminomethyl)4-nitrophenol of formula (III) with a halogen acetamide to form the 2-(2-N-acylaminomethyl4-nitrophenoxy)-acetamide of formula (IV);

b) converting the 2-(2-N-acylaminomethyl-4-nitrophenoxy)-acetamide of formula (IV) to the 2-(N-acylaminomethyl)-4-nitroaniline of formula (V);

c) reducing the 2-(N-acylaminomethyl)-4-nitroaniline to form the 1,4-diamino-2-(N-acylaminomethyl)benzene of formula (VI);

d) adding hydrochloric acid to deacylate the 1,4-diamino-2-(N-acyl-aminomethyl)benzene of formula (VI) and form the corresponding trichloride of formula VII; and e) when n=0 subsequently converting to the free base form of formula I; or when n≠0 respectively converting to a corresponding salt of HX of formula (1), with the proviso that HX is not HCl when n=3.

Either inorganic or organic acids can be used as the acid ingredient in the above process according to the invention. However the following acids are preferred: hydrochloric acid, sulfuric acid, boric acid, citric acid and tartaric acid. Hydrochloric and sulfuric acid are especially preferred.

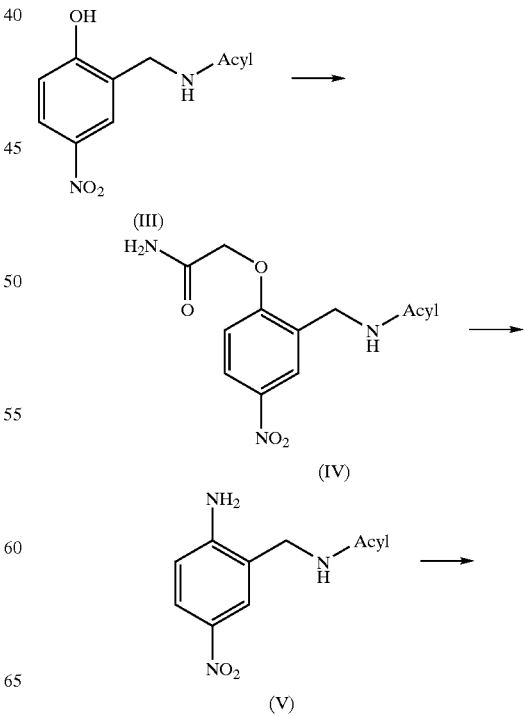

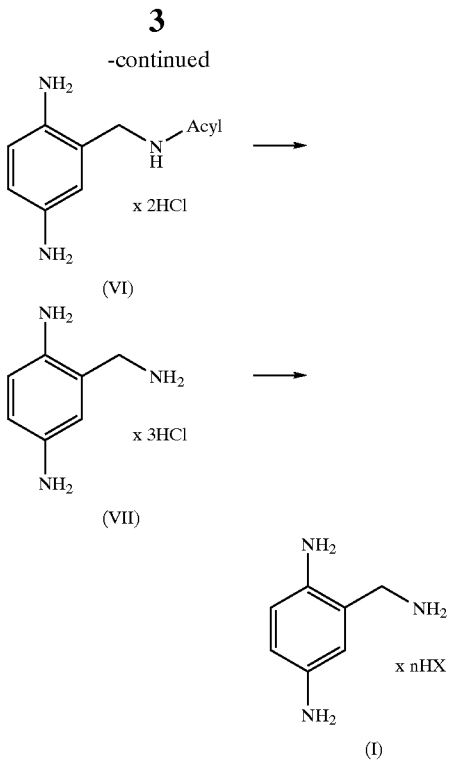

The aminomethylation of 2-(N-acylaminomethyl)-4-nitrophenol of formula (III) was described by H. E. Zaugg, Synthesis 1984, pp. 85 to 96. Starting from this intermediate the easily accessible 2-(2-N-acylaminomethyl-4-nitrophenoxy)-acetamide of formula (IV) is produced by heating with a halogen acetamide. Iodoacetamide and the somewhat less reactive bromoacetamide are ideally suited as the halogen acetamide. When the more economical chloroacetamide is used to reduce costs, it is advantageous to catalyze the reaction with an iodide, especially sodium iodide or potassium iodide. The amount of the iodide that will result in a higher reaction rate is considerably more than 10% (molar); 50% (molar) has proven to be suitable throughout. The reaction can be performed easily in the usual manner in a normal dipolar aprotic solvent under reflux temperature. The dipolar aprotic solvent can be, for example, acetone. Dialkyl ethers of ethylene glycols and their homologs, preferably those with boiling points under 200° C., such as ethylene glycol dimethyl ether, are suitable as additional solvents. The rearrangement to 2-(N-acylaminomethyl)-4-nitroaniline of formula (V) occurs subsequently by addition of base in a solvent, such as dimethylformamide, dimethylacetamide or N-methyl-pyrrolidone, analogously to the reaction described in W. R. Baker, J. Org. Chem. 48, 5140 (1983). Besides the bases disclosed in this reference carbonates, such as sodium carbonate or potassium carbonate, can be used as the added base. Since the carbonates are present in a suspension under the conditions of this latter reaction, it is advantageous to provide it as a fine powder and to use it in a two to five fold excess. The powder should be as fine as possible. The reaction can be performed in a wide temperature range. At temperatures below 80° C. the conversion is low, while at temperatures above 140° C. the reaction mixture is darkly colored by by-products, so that the preferred temperature is in a range from 80 to 120° C. The compound of formula (V) is subsequently reduced in an ideal manner according to the conventional method in an ideal way by catalytic hydrogenation with slightly elevated hydrogen pressure or at slightly elevated temperatures. In this catalytic hydrogenation reaction the compound of formula (V) is converted into the 1,4-diamino-2-(N-acylaminomethyl)benzene dihydrochloride of formula (VI). Finally the compound of formula (VI) is deacylated with hydrochloric acid and the 2-aminomethyl-1,4-diaminobenzene is precipitated as the trichloride of formula (VII). This acid adduct may then be easily converted into the free base form or into other salt adducts of the general formula (I). Understandably also one of the intermediates, for example formula (V), could also be used.

Because of the high oxidation sensitivity of the above-mentioned free base form of the compound of formula (I) (n=0) it is preferably isolated as the acid adduct (n≠0) of formula (VII). The trihydrochloride is a special case of the general formula (I) in which n=3 and HX=HCl.

The compounds of formula (I) are outstanding as oxidation dye-precursor compounds for dyeing keratin fibers.

The present invention also includes compositions and methods for dyeing keratin fibers, especially wool, silk or hair, particularly human hair, using the compounds of formula (I).

Although the compounds of formula (I) are especially suitable for dyeing keratin fibers, in principle it would also be possible to dye other natural or synthetic fibers, especially cotton or nylon 66, with these compounds.

The compounds of formula (I) can be used both alone and also in combination with-certain known developer substances and/or coupler substances, generally known for dyeing fiber materials in oxidative dye systems.

The following compounds especially are suitable coupler substances: N-(3-dimethylaminophenyl)urea, 2,6-diaminopyridine, 2-amino-4-[(2-hydroxyethyl)amino] anisole, 2,4-diamino-1-fluoro-5-methylbenzene, 2,4-diamino-1-methoxy-5-methylbenzene, 2,4-diamino-1-ethoxy-5-methyl-benzene, 2,4-diamino-1-(2-hydroxyethoxy)-5-methylbenzene, 2,4-di-[(2-hydroxyethyl)amino]-1,5-dimethoxybenzene, 2,3-diamino-6-methoxypyridine, 3-amino-6-methoxy-2-(methylamino)-pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1-(3-hydroxypropoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)-amino]aniline, 1,3-di(2,4-diaminophenoxy)propane, di-(2,4-diaminophenoxy)-methane, 1,3-diamino-2,4-dimethoxybenzene, 2,6-bis-(2-hydroxyethyl)-aminotoluene, 4-hydroxyindol, 3-dimethylaminophenol, 3-diethylaminophenol, 5-amino-2-methylphenol, 5-amino-4-fluoro-2-methylphenol, 5-amino4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methyl-phenol, 3-amino-phenol, 2-[(3-hydroxyphenyl)amino]acetamide, 5-[(2-hydroxy-ethyl)amino]-2-methylphenol, 3-[(2-hydroxyethyl)amino]-phenol, 3-[(2-methoxy-ethyl)amino]-phenol, 5-amino-2-ethylphenol, 2-(4-amino-2-hydroxyphenoxy)-ethanol, 5-[(3-hydroxypropyl)amino]-2-methylphenol, 3-[(2,3- dihydroxypropyl)-amino]-2-methyl-phenol, 3-[(2-hydroxyethyl )amino]-2-methylphenol, 2-amino-3-hydroxypyridine, 5-amino-4-chloro-2-methylphenol, 1-naphthol, 1,5-dihydroxy-naphthalene, 1,7-dihydroxynaphthalene, 2,3-dihydroxynaphthalene, 2,7-dihydroxynaphthalene, 2-methyl-1-naphthol acetate, 1,3-dihydroxy-benzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylene-dioxyphenol, 3,4-methylenedioxy-aniline, 5-[(2-hydroxyethyl)amino]-1,3-benzodioxole, 6-bromo-1-hydroxy-3,4-methylendioxybenzene, 3,4-diamino-benzoic acid, 3,4-dihydro-6-hydroxy-1,4(2H)-benzoxazine, 6-amino-3,4-dihydro-1,4(2H)-benzoxazine, 3-methyl-1-phenyl-5-pyrazoleone, 5,6-dihydroxyindole, 5,6-dihydroxyindoline, 5-hydroxyindole, 6-hydroxyindole, 7-hydroxyindole and 2,3-indolindione, or their salts.

To produce particularly natural shades and fashionable red tones it is especially advantageous to use the compounds of formula (I) in combination with additional developer substances. The follow compounds may be considered as the developer substances: para-phenylenediamine, para-aminophenols and 4,5-diaminopyrazoles, or their salts. The following compounds are especially suitable as developer compounds: 1,4-diaminobenzene (p-phenylendiamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)amino]aniline, 4-[(2-methoxyethyl)-amino]-aniline, 4-[(3-hydroxypropyl)amino]aniline, 1,4-diamino-2-(2-hydroxy-ethyl)benzene, 1,4-diamino-2-(1-methylethyl)benzene, 1,3-bis-[(4-aminophenyl)-(2-hydroxyethyl)amino]-2-propanol, 1,8-bis-(2,5-diaminophenoxy)-3,6-dioxaoctane, 4-aminophenol, 4-amino-3-methylphenol, 4-methylaminophenol, 4-amino-2-(aminomethyl)phenol, 4-amino-2-[(2-hydroxyethyl)amino]methylphenol, 4-amino-2-(methoxymethyl)phenol, 4-amino-2-(2-hydroxyethyl)phenol, 5-amino-salicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-aminophenol, 2-amino6-methylphenol and 2-amino-5-methylphenol, or their salts.

The compounds of formula (I) can also understandably be used in combination with various direct-dyeing anionic, cationic or neutral dye compounds. The following are preferred examples of anionic dye direct-dyeing dye compounds for use in the compositions of the invention: 6-hydroxy-5-[(4-sulfophenyl)azo]-2-naphthalene sulfonic acid disodium salt (C.I. 15985; Food Yellow No. 3; FD&C Yellow No. 6), 2,4-dinitro-1-naphthol-7-sulfonic acid disodium salt (C.I.10316; Acid Yellow No. 1; Food Yellow No. 1), 2-(indan-1,3-dion-2-yl)quinoline-x,x-sulfonic acid (mixture of mono- and disolfuonic acid) (C.I.47005;D&C Yellow No. 10; Food Yellow No. 13, Acid Yellow No. 3), 5-hydroxy-1-(4-sulfophenyl )4-[(4-sulfophenyl )azo] pyrazole-3-carboxylic acid sodium salt (C.I. 19140; Food Yellow No. 4; Acid Yellow No. 23), 9-(2-carboxyphenyl)-6-hydroxy-3H-xanthen-3-one (C.I.45350; Acid Yellow No. 73; D&C Yellow No. 8), 5-[(2,4-dinitrophenyl)amino]-2-phenylaminobenzenesulfonic acid sodium salt (C.I.10385; Acid Orange No. 3), 4-[(2,4-dihydroxyphenyl)azo]-benzene sulfonic acid monosodium salt (C.I.14270; Acid Orange No. 6), 4-[(2-hydroxynaphth-1-yl)azo]benzenesulfonic acid sodium salt (C.I. 15510; Acid Orange No. 7), 4-[(2,4-dihydroxy-3-[(2,4-dimethylphenyl)azo]phenyl)azo]-benzene sulfonic acid sodium salt (C.I.20170; Acid Orange No. 24), 4-hydroxy-3-[(4-sulfonaphth-1-yl)azo]-1-naphthalene sulfonic acid disodium salt (C.I.14720; Acid Red No.14), 6-hydroxy-5-[(4-sulfonaphth-1-yl)azo]-2,4-naphthalene-disulfonic acid trisodium salt (C.I. 16255; Ponceau 4R; Acid Red No. 18), 3-hydroxy4-[(4-sulfonaphth-1-yl)azo]-2,7-naphthalene-disulfonic acid trisodium salt (C.I. 16185; Acid Red No. 27), 8-amino-1-hydroxy-2-(phenylazo)-3,6-naphthalene disulfonic acid disodium salt (C.I.17200; Acid Red No. 33), 5-(acetylamino)-4-hydroxy-3-[(2-methylphenyl)azo]-2,7-naphthalene disulfonic acid disodium salt (C.I.18065; Acid Red No. 35), 2-(3-hydroxy-2,4,5,7-tetraiodo-dibenzopyran-6-on-9-yl)-benzene sulfonic acid disodium salt (C.I. 45430; Acid Red No. 51), N-[6-(diethylamino)-9-(2,4-disulfophenyl)-3H-xanthen-3-yliden]-N-ethylethanaminium hydroxide, inner Salt, sodium salt (C.I.45100; Acid Red No. 52), 8-[(4-(phenylazo)phenyl) azo]-7-naphthol-1,3-disulfonic acid disodium salt (C.I. 27290; Acid Red No. 73), 2',4',5',7'-tetrabromo-3',6'-dihydroxy-spiro[isobenzofuran-1-(3H),9'-[9H]xanthen]-3-one disodium salt (C.I.45380; Acid Red No. 87), 2',4',5',7'-tetrabromo-4,5,6,7-tetrachloro-3',6'-dihydroxy-spiro [isobenzofuran-1(3H),9'[9H]xanthen]-3-one disodium salt (C.I. 45410; Acid Red No. 92), 3',6'-dihydroxy-4',5'-diiodospiro[isobenzofuran-1(3H),9'(9H)-xanthen)-3-one disodium salt (C.I. 45425; Acid Red No. 95), (2-sulfophenyl)-di-[4-(ethyl-((4-sulfophenyl)methyl)amino) phenyl]carbenium disodium salt, betaine (C.I. 42090; Acid Blue No. 9; FD&C Blue No. 1), 1,4-bis-[(2-sulfo-4-methylphenyl)amino]-9,10-anthraquinone disodium salt (C.I. 61570; Acid Green No. 25), bis-[4-(dimethylamino)phenyl]-(3,7-disulfo-2-hydroxynaphth-1-yl)carbenium, inner salt, monosodium salt (C.I. 44090; Food Green No. 4; Acid Green No. 50), bis-[4-(diethylamino)phenyl](2,4-disulfophenyl)carbenium inner salt, sodium salt (2:1) (C.I. 42045; Food Blue No. 3; Acid Blue No. 1), bis[4-(diethylamino)phenyl]-(5-hydroxy-2,4-disulfophenyl) carbenium inner salt, calcium salt (2:1) (C.I. 42051; Acid Blue No. 3), 1-amino4-(cyclohexylamino)-9,10-anthraquinone-2-sulfonic acid sodium salt (C.I. 62045; Acid Blue No. 62), 2-(1,3-dihydro-3-oxo-5-sulfo-2H-indol-2-yliden)-2,3-dihydro-3-oxo-1H-indol-5-sulfonic acid disodium salt (C.I. 73015; Acid Blue No. 74), 9-(2-carboxyphenyl)-3-[(2-methylphenyl)-amino]6-[(2-methyl-4-sulfophenyl)amino]xanthylium inner salt, monosodium salt (C.I. 45190; Acid Violet No. 9), 1-hydroxy-4-[(4-methyl-2-sulfophenyl)amino]-9,10-anthraquinone sodium salt (C.I. 60730; D&C Violet No. 2; Acid Violet No. 43), bis-[3-nitro4-[(4-phenylamino)-3-sulfophenylamino] phenyl]-sulfone (C.I. 10410; Acid Brown No.13), 5-amino-4-hydroxy6-[(4-nitrophenyl)azo]3-(phenylazo)-2,7-naphthalene disulfonic acid disodium salt (C.I.20470; Acid Black No. 1), 3-hydroxy4-[(2-hydroxynaphth-1-yl)azo]-7-nitronaphthalenesulfonic acid chromium complex (3:2) (C.I. 15711; Acid Black No. 52), 3-[(2,4-dimethyl-5-sulfophenyl) azo]4-hydroxy-1-naphthalenesulfonic acid disodium salt (C.I. 14700; Food Red No. 1; Ponceau SX; FD&C Red No. 4), 4-(acetylamino)-5-hydroxy-6-[(7-sulfo-4-[(4-sulfophenyl)azo]naphth-1 yl)azo]-1,7-naphthalene disulfonic acid tetrasodium salt (C.I. 28440; Food Black No. 1), 3-hydroxy-4-(3-methyl-5-oxo-1-phenyl-4,5-dihydro-1H-pyrazole-4-yl-azo)-naphthalene-1-sulfonic acid sodium salt chromium complex (Acid Red No. 195).

The following are preferred cationic direct-dyeing dye compounds: 9-(dimethylamino)benzo[a]phenoxazin-7-ium chloride (C.I. 51175; Basic Blue No. 6), di[4-(diethylamino) phenyl][4-(ethylamino)naphthyl]carbenium chloride (C.I. 42595; Basic Blue No. 7), 3,7-di(dimethylamino) phenothiazin-5-ium chloride (C.I. 52015; Basic Blue No. 9), di[4-dimethylamino)phenyl][4(phenylamino)-naphthyl] carbenium chloride (C.I. 44045; Basic Blue No. 26), 2-[(4-(ethyl(2-hydroxyethyl)amino)phenyl)azo]-6-methoxy-3-methylbenzothiazolium methylsulfate (C.I. 11154; Basic Blue No. 41), 8-amino-2-bromo-5-hydroxy-4-imino6-[(3-(trimethylammonio)phenyl)amino]-1(4H)naphthalenone chloride (C.I.56059; Basic Blue No. 99), bis-[4-(dimethylamino)phenyl][4-(methylamino)-phenyl] carbenium chloride (C.I. 42535; Basic Violet No. 1), tris-(4-amino-3-methylphenyl)carbenium chloride (C.I. 42520; Basic Violet No.2), tris-[4-(dimethylamino)phenyl] carbenium chloride (C.I. 42555; Basic Violet No. 3), 2-[3, 6-(diethylamino)dibenzopyranium-9-yl]benzoic acid chloride (C.I. 45170; Basic Violet No. 10), di(4-aminophenyl) (4-amino-3-methylphenyl)carbenium chloride (C.I. 42510; Basic Violet No.14), 1,3-bis[(2,4-diamino-5-methylphenyl)-azo]-3-methylbenzene (C.I. 21010;Basic Brown No. 4), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (C.I. 12251; Basic Brown No. 17), 1-[(4-amino-3-nitrophenyl)azo]-7-(trimethylammonio)-2-naphthol chloride (C.I. 12251; Basic Brown No. 17), 3,7-diamino-2, 8-dimethyl-5-phenylphenazinium chloride (C.I. 50240; Basic Red No. 2), 1,4-dimethyl-5-[(4(dimethylamino) phenyl)azo]-1,2,4-triazolium chloride (C.I. 11055; Basic Red No. 22), 2-hydroxy-1-[(2-methoxyphenyl)azo]-7-(trimethylammonio)-naphthalene chloride (C.I. 12245; Basic Red No. 76), 2-[2-((2,4-dimethoxy-phenyl)amino) ethenyl]-1,3,3-trimethyl-3H-indol-1-ium-chloride (C.I. 48055; Basic Yellow No. 11), 3-methyl-1-phenyl-4-[(3-(trimethylammonio)phenyl)azo]-pyrazole-5-one chloride (C.I. 12719; Basic Yellow No. 57), bis-[4-(diethylamino) phenyl]phenylcarbenium hydrogen sulfate(1:1) (C.I. 42040; Basic Green No. 1).

To improve the color balance and to produce special shades the following nonionic direct-dyeing dye compounds have proven to be especially useful in the compositions according to the invention: 1-amino-2-[(2-hydroxyethyl) amino]-5-nitrobenzene (HC Yellow No. 5), 1-(2-hydroxyethoxy)-2-[(2-hydroxyethyl)-amino]-5-nitrobenzene (HC Yellow No. 4), 1-[(2-hydroxyethyl) amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino4-nitrobenzene, 2-[(2-hydroxy-ethyl)amino]-5-nitrophenol (HC Yellow No. 11), 3-[(2-aminoethyl)amino]-1-methoxy4-nitrobenzene hydrochloride (HC Yellow No.9), 1-[(2-ureidoethyl)-amino]-4-nitrobenzene, 4-[(2, 3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro4-[(2-hydroxyethyl)amino]-3-nitrobenzene (HC Yellow No. 12), 4-[(2-hydroxyethyl) amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1-amino4-[(2-hydroxyethyl)amino]-2-nitrobenzene (HC Red No. 7), 2-amino4,6-dinitrophenol, 2-ethylamino4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2hydroxyethyl) amino]-2-nitrobenzene, 4-amino-1-[(2-hydroxyethyl) amino]-2-nitrobenzene (HC Red No 3), 4-amino-3-nitrophenol, 4-[(2-hydroxyethyl)amino]-3-nitrophenol, 1-[(2-ami noethyl )amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2, 3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]-benzoic acid, 2-chloro-6-methylamino4-nitrophenol 2-chloro-6-[(2-hydroxyethyl) amino]-4-nitrophenol, 2-chloro-6-ethylamino4-nitrophenol, 2-amino-6-chloro4-nitrophenol, 4-[(3-hydroxypropyl) amino]-3-nitrophenol, 2,5-diamino-6-nitropyridine, 1,2,3,4-tetrahydro-6-nitrochinoxalin, 7-amino-3,4-dihydro6-nitro-2H-1,4-benzoxazine (HC Red No. 14),1,4-bis-[(2-hydroxyethyl)amino]-2-nitrobenzene, 1-(2-hydroxyethyl) amino-2-nitro-4-[di(2-hydroxyethyl)amino]benzene (HC Blue No. 2), 1-amino-3-methyl4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxy-propyl) amino]-4-[methyl-(2-hydroxyethyl)-amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)4-[di(2-hydroxyethyl)amino]-2-nitrobenzene (HC Violet No. 2), 1-methylamino-4-[methyl-(2,3-dihydroxypropyl)amino]-2nitrobenzene (HC Blue No. 6), 2-((4-amino-2-nitrophenyl) amino)-5-dimethylamino-benzoic acid (HC Blue No. 13), 1,4-di[(2,3-dihydroxypropyl)amino]-9,10-anthraquinone, 1-[(2-hydroxyethyl)amino]4-methylamino-9,10- anthraquinone (C.I.61505, disperse Blue No. 3), 2-[(2-aminoethyl)amino]-9,10-anthraquinone (HC Orange No. 5), 1-hydroxy4-[(4-methyl-2-sulfophenyl)amino]-9,10-anthraquinone, 1-[(3-aminopropyl)amino]4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (C.I.62015, disperse Red No. 11, Solvent Violet No. 26), 1,4-dihydroxy-5,8-bis[(2-hydroxyethyl)amino-9,10-anthraquinone (C.I. 62500, disperse Blue No. 7, Solvent Blue No. 69), 1-[di-(2-hydroxyethyl)amino]-3-methyl-4-[(4-nitrophenyl)azo] benzene (C.I. 11210, disperse Red No. 17), 4-[(4-aminophenyl)azo]-1-[di(2-hydroxyethyl)amino]-3-methylbenzene (HC Yellow No. 7), 2,6-diamino-3-[(pyridine-3-yl)azo]pyridine, 2-((4-(acetylamino)phenyl)azo)4-methylphenol (C.I. 11855; disperse Yellow No. 3).

From the group of direct-dyeing dye compounds the following compounds have a special significance: 2-amino-4,6-dinitrophenol, 2-ethylamino4,6-dinitrophenol, 2-[(2-hydroxyethyl)amino]-4,6-dinitrophenol and dye compounds of the following general formula (VIII):

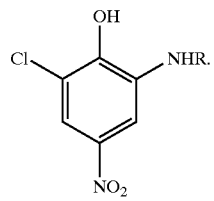

(VIII)

wherein R represents hydrogen, methyl, ethyl or hydroxyethyl.

The above-described combination according to the invention of the compounds of formula (1) with oxidation dye precursor compounds and/or direct-dyeing dye compounds is applied to the fibers to be dyed in a suitable dye-carrying composition.

The present invention also includes ready-to-apply hair dye mixtures for oxidative dyeing of hair, which are each made by mixing an oxidation dye precursor composition with an oxidizing agent immediately prior to application. They are characterized by a content of at least one compound of formula (I) as well as additional oxidation dye precursor compounds and/or direct-dyeing dye compounds as needed.

The compounds of formula (I) and the oxidation dye precursor compounds are contained in the compositions of the invention in total amounts of about 0.01 to 10 percent by weight respectively, preferably from 0.2 to 6 percent by weight. The total concentration of direct-dyeing dye compounds in the compositions according to the invention amounts to about 0.1 to 10 percent by weight respectively, preferably from 0.1 to 5 percent by weight.

Furthermore antioxidants, perfume oils, complex formers, wetting agents, emulsifiers, penetration agents, buffer systems, preservatives, thickeners, care materials and other cosmetic additives may be present in the dye-carrying or oxidation dye precursor composition according to the invention.

The form of the oxidation dye precursor composition and also for the ready-to-apply dye mixture can be, for example, a solution, especially an aqueous or aqueous-alcoholic solution. However the particularly preferred form of the composition according to the invention is a cream, a gel or an emulsion. Its composition comprises a mixture of the dye ingredients with the conventional additive ingredients usually used in this type of preparation.

The conventional additive ingredients for solutions, creams, emulsion or gels are, for example, solvents, such as water, lower aliphatic alcohols, for example ethanol, n-propanol and isopropanol or glycols, such as glycerol and 1,2-propylene glycol; wetting agents or emulsifiers from the classes of anionic, cationic, amphoteric or nonionic surface-active substances, such as fatty alcohol sulfates, ethoxylated fatty alcohol sulfates, alkyl sulfonates, alkyl benzene sulfonates, alkyltrimethylammonium salts, alkyl betaines, ethoxylated fatty alcohols, ethoxylated nonylphenols, fatty acid alkanol amides, fatty acid esters; thickeners, such as higher fatty alcohols, starches or cellulose derivative compounds, petrolatum (Vaseline®), paraffin oils and fatty acids and furthermore care materials, such as cationic resins, lanolin derivative compounds, cholesterol, pantothenic acid and betain. The above-mentioned ingredients are included in the compositions according to the invention in respective amounts suitable for their purposes. For example, the wetting agents and emulsifiers are contained in the compositions according to the invention in concentrations of about 0.5 to 30 percent by weight, the thickeners in amounts of from about 0.1 to 25 percent by weight and the care materials in a concentration of about 0.1 to 5.0 percent by weight.

The ready-to-apply hair dye mixture according to the invention is made by a method comprising mixing the oxidation dye precursor composition with a liquid oxidizing agent immediately prior to application.

Hydrogen peroxide, or its addition compounds with urea, melamine or sodium bromate, in the form of a 1 to 12 percent by weight, preferably 6 percent by weight, aqueous solution, is preferred as the oxidizing agent. Hydrogen peroxide is especially preferred.

The oxidation dye precursor composition and the oxidizing agent are mixed with each other inma weight ratio of from 5:1 to 1:3. A weight ratio of 1:1 to 1:2 is especially preferred.

The pH of the ready-to-apply hair dye mixture according to the invention is adjusted during the mixing of the preferred alkaline oxidation dye precursor composition with the mostly acidic oxidizing agent. The resulting pH value of the mixture is determined by the alkali content of the dye-carrying or oxidation dye precursor composition, the acid content of the oxidizing agent and the mixing ratio. The pH of the ready-to-apply hair dye composition amounts to about 3 to 11, preferably between 6 and 10.5.

The pH values of both the oxidation dye precursor composition and the oxidizing agent-containing composition can both be adjusted by adding dilute organic or inorganic acids, such as phosphoric acid, ascorbic acid and lactic acid, or bases, such as monoethanolamine, triethanolamine, 2-amino-2-methyl-1-propanol, ammonia, sodium hydroxide, potassium hydroxide or tris(hydroxy-methyl) aminomethane.

After mixing the above-described oxidation dye precursor composition with an oxidizing agent, an amount of the ready-to-apply hair dye mixture sufficient for dyeing the hair, generally from about 60 to 200 grams, is applied to the hair.

The hair dye mixture is allowed to act on the hair after application for about 10 to 45 minutes at 15 to 50° C., preferably for 30 minutes at 40° C. It is subsequently rinsed from the hair with water. If necessary the hair is washed with a shampoo after rinsing with water and perhaps with a dilute weak organic acid, for example citric or tartaric acid. Subsequently the hair is dried.

The following examples illustrate the above-described invention, but without however limiting the broad concept of the invention.

EXAMPLES

Example 1

Preparation of 2-aminomethyl-1,4-diaminobenzene Trihydrochloride

Step 1: 2-(N-acetylaminomethyl) 4-nitrophenoxyacetamide 131.4 g of 2-acetylaminomethyl-4-nitrophenol, 64.4 g of chloroacetamide, 86.4 g of calcium carbonate and 57.1 g of potassium iodide in 800 ml of acetone are heated under reflux for four hours. Subsequently the reaction mixture is cooled to room temperature and poured into 1300 ml of water. The resulting precipitate is filtered, washed with water and subsequently dried. 120 g of a yellow product are obtained having a melting point of from 236 to 240° C.

CHN analysis ($C_{11}H_{13}N_3O_5$; MW=267.24)

|  | % C | % H | % N |
|---|---|---|---|
| Calculated: | 49.44 | 4.90 | 15.72 |
| Found: | 49.22 | 4.93 | 15.70 |

Step 2: 2-( N-acetylaminomethyl)-4-nitroaniline 120 g of the 2-(N-acetylaminomethyl)-4-nitrophenoxyacetamide made in step 1 are dissolved in 450 ml of N-methylpyrrolidone, mixed with 155 g of potassium carbonate and heated for 4.5 hours at 100° C. Subsequently the reaction mixture is cooled to room temperature, diluted with 840 ml of ethyl acetate, filtered and the solvent is evaporated in vacuum at 60 to 80° C. The remaining residue is crystallized by addition of ethanol. The product is filtered with suction, taken up in 250 ml ethanol and heated briefly under reflux. Subsequently the solution is cooled, filtered and the residue is dried in vacuum. 46.6 g of a yellow powder are obtained with a melting point of 208 to 210° C.

Step 3: 2-(N-acetylaminomethyl)-1,4-diaminobenzene Dihydrochloride 25 g of the 2-(N-acetylaminomethyl)-4-nitroaniline from step 2 are dissolved in 250 ml ethanol, mixed with 2.5 g palladium (10% in activated carbon) and hydrogenated under mildly elevated hydrogen pressure. After about 5 hours the hydrogen uptake has ended and a colorless solution is obtained after removal of the catalyst by filtration.

The 2-(N-acetylaminomethyl)-1,4-diaminobenzene dihydrochloride is precipitated by addition of the required amount of a saturated solution of HCl in ethanol for salt formation. The precipitate is filtered with suction, washed with a little ethanol and dried in vacuum. 20.2 g of colorless crystals result with a melting point of over 215° C. (with decomposition).

Step 4: 2-aminomethyl-1,4-diaminobenzene Trihydrochloride 17 g of the dihydrochloride from step 3 are heated in 50 ml ethanol and 20 ml of concentrated hydrochloric acid at 70° C. A thick suspension of the product is generally obtained. After 3.5 hours the reaction mixture is cooled to room temperature, the residue is filtered with suction and well pressed. After drying one obtains 12.5 g colorless hygroscopic crystals with a melting point of 246 to 248° C.

$^1$H-NMR ($D_2O$): δ=4.27 ppm(s,2H); 7.30 ppm (d, $^3J_{HH}$=8.55 Hz,1H); 7.42 ppm (dd, $^3J_{HH}$=8.55 Hz, $^4J_{HH}$=2.60 Hz,1 H); 7.46 ppm (d, $^4J_{HH}$=2.60 Hz,1)

CHNCl analysis ($C_7H_{11}N_3$×2.95HCl; MW=246.57)

Accounting for the presence of 6.54% residual water

|  | % C | % H | % N | % Cl |
|---|---|---|---|---|
| Calculated: | 32.11 | 6.10 | 16.05 | 39.94 |
| Found: | 32.3 | 6.00 | 16.1 | 39.9 |

Example 2

Preparation of 2-aminomethyl-1,4-diaminobenzene Disulfate 3 g of the 2-aminomethyl-1,4-diaminobenzene trihydrochloride made in step 4 of example 1 are stirred into concentrated sulfuric acid. Hydrogen chloride gas escapes and a viscose mass is formed. After two hours the reaction mixture is carefully cooled with weak cooling and diluted in 50 ml ethanol. A fine suspension is obtained which is subsequently stirred for one hour at room temperature. The precipitate is filtered with suction and subsequently washed with a little ethanol. 2.7 g of a bright gray powder are obtained with with a melting point of 242 to 244° C.

$^1$H-NMR (DMSO-$d_6$): δ=3.92 ppm(s,2H); 6.83 ppm (d, $^3J_{HH}$=8.55 Hz,1H); 7.01 ppm (d, $^3J_{HH}$=8.85 Hz, 1H); 7.04 ppm (s broadened, 1H)

CHNS analysis ($C_7H_{11}N_3$×2 $H_2SO_4$; MW=333.35)

Accounting for the presence of 0.5 Mol % residual water and 0.1 Mol % ethanol:

|  | % C | % H | % N | % S |
|---|---|---|---|---|
| Calculated: | 24.92 | 4.82 | 12.11 | 18.48 |
| Found: | 25.40 | 4.70 | 11.90 | 18.60 |

Example 3
Hair Dye Precursor Composition, Basic Cream

| | |
|---|---|
| 15.00 g | cetyl stearyl alcohol (50/50) |
| 5.00 g | glycerol monostearate |
| 2.00 g | cocamide DEA |
| 10.00 g | sodium lauryl ether sulfate, 28% aqueous solution |
| 0.30 g | ascorbic acid |
| 0.40 g | sodium sulfite |
| 4.50 g | ammonia, 25% aqueous solution |
| 0.56 g | 2-aminomethyl-1,4-diaminobenzene trihydrochloride |
| X g | coupler substance from Table I |
| to 100.00 g | water, demineralized. |

The pH of the cream is between 10 and 10.5.

Immediately prior to application 100 g of the above-described oxidation dye precursor composition is mixed with 100 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The obtained color shades and color intensities are summarized in Table I.

| | |
|---|---|
| 0.30 g | sodium sulfite |
| 5.15 g | ammonia, 25% aqueous solution |
| 0.10 g | 5-((2-hydroxyethyl)amino-1,3-benzodioxole hydrochloride |
| 1.65 g | 2-aminomethyl-1,4-diaminobenzene disulfate |
| 0.26 g | 2-methylresorcinol |
| 0.29 g | 2-amino-6-chloro-4-nitrophenol hydrochloride |
| 0.70 g | 5-amino-2-methylphenol |
| 0.33 g | 1,4-diamino-2-(2-hydroxyethyl)benzene sulfate |
| 0.43 g | 1,4-diamino-2-methylbenzene sulfate |
| to 100.00 g | water, demineralized. |

The pH of the cream is 10.2.

Immediately prior to application 100 g of the above-described oxidation dye precursor composition is mixed with 100 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The dyed hair color is brown with reddish reflections.

TABLE I

HAIR DYE PRECURSOR COMPOSITIONS CONTAINING 2-AMINOMETHYL-1,4-DIAMINOBENZENE TRIHYDROCHLORIDE

| Example | Coupler Compound | Color Shade | Intensity |
|---|---|---|---|
| 3a | 0.28 g resorcinol | Medium blond | (++) |
| 3b | 0.27 g 3-aminophenol | Aubergine | (O) |
| 3c | 0.31 g 5-amino-2-methylphenol | Red-violet | (++) |
| 3d | 0.64 5-((2-hydroxyethyl)amino)-2-methoxyaniline dihydrochloride | Bluish-black | (++) |
| 3e | 0.47 g 6-amino-3,4-dihydro-2H-1,4-benzoxazine hydrochloride | Blue | (++) |
| 3f | 0.59 g 1,3-diamino-4-methoxybenzene sulfate | Blue | (++) |
| 3g | 0.36 g 1-chloro-2,4-dihydroxybenzene | Gold | (++) |
| 3h | 0.57 g 3-amino-6-methoxy-2-(methyl-amino)pyridine hydrochloride | Aubergine | (++) |
| 3I | 0.35 g 5-hydroxy-1,3-benzodioxole | Chestnut | (++) |
| 3j | 0.43 g 5-amino-1,3-benzodioxole hydrochloride | Dark brown | (++) |
| 3k | 0.44 g 4-methoxy-1-naphthol | Blue-violet | (O) |
| 3l | 0.61 g 3,5-diamino-2,6-dimethoxy-pyridine dihydrochloride | Bluish-black | (++) |
| 3m | 0.40 g 1,7-dihydroxynaphthalene | Blue-violet | (O) |
| 3n | 0.31 g 1,3-dihydroxy-2-methylbenzene | Red-brown | (+) |
| 3o | 0.45 g 3-dimethylaminophenylurea | Turquoise | (++) |
| 3p | 0.33 g 4-hydroxyindole | Red-violet | (++) |
| 3q | 0.39 g 3-amino-2-chloro-6-methylphenol | Violet | (++) |
| 3r | 0.56 g 2-chloro-5-((2,2,2-trifluoro-ethyl)amino)phenol | Gray-blue | (+) |
| 3s | 0.45 g 3-amino-2,4-dichlorophenol | Blue-black | (++) |
| 3t | 0.36 g 5-amino-2-chlorophenol | Red-brown | (+) |

(O) = average, (+) intense; (++) = very intense

Example 4
Hair Dye Precursor Composition, Basic Cream

| | |
|---|---|
| 15.00 g | cetyl stearyl alcohol (50/50) |
| 5.00 g | glycerol monostearate |
| 2.00 g | cocamide DEA |
| 10.00 g | sodium lauryl ether sulfate, 28% aqueous solution |
| 0.30 g | ascorbic acid |

Example 5
Hair Dye Precursor Composition, Acidic Cream

| | |
|---|---|
| 15.00 g | cetyl stearyl alcohol (50/50) |
| 5.00 g | glycerol monostearate |
| 2.00 g | cocamide DEA |
| 10.00 g | sodium lauryl ether sulfate, 28% aqueous solution |
| 0.30 g | ascorbic acid |

-continued

| | | |
|---|---|---|
| 0.40 g | sodium sulfite | |
| 0.56 g | 2-aminomethyl-1,4-diaminobenzene trihydrochloride | |
| X g | coupler substance from Table II | |
| to 100.00 g | water, demineralized. | |

Immediately prior to application 100 g of the above-described oxidation dye precursor composition is mixed with 100 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The obtained color shades and color intensities are summarized in Table II together with the pH values.

TABLE II

HAIR DYE PRECURSOR COMPOSITIONS CONTAINING
2-AMINOMETHYL-1,4-DIAMINOBENZENE-TRIHYDROCHLORIDE

| Example | Coupler | pH Value | Color Shade | Intensity |
|---|---|---|---|---|
| 5a | 0.28 g resorcinol | 6.6 | Brown | (+) |
| 5b | 0.27 g 3-aminophenol | 5.8 | Medium blond | (o) |
| 5c | 0.31 g 5-amino-2-methylphenol | 6.6 | Red-violet | (+) |
| 5d | 0.64 5-((2-hydroxy-ethyl)amino)-2-methoxyaniline dihydrochloride | 6.7 | Blue | (+) |

(o) = average, (+) = intense; (++) = very intense

Example 6

Oxidation Hair Dye Precursor Composition in Gel Form

| | |
|---|---|
| 15.00 g | oleic acid |
| 3.00 g | glycerol |
| 7.00 g | isopropanol |
| 0.50 g | ascorbic acid |
| 0.40 g | sodium sulfite |
| 0.40 g | sodium hydroxide |
| 10.00 g | ammonia, 25% aqueous solution |
| 0.56 g | 2-aminomethyl-1,4-diaminobenzene trihydrochloride |
| X g | coupler substance from Table III |
| to 100.00 g | water, demineralized. |

Immediately prior to application 100 g of the above-described oxidation dye precursor composition is mixed with 100 grams of a 6% by weight aqueous hydrogen peroxide solution. The resulting ready-to-use hair dye mixture is applied to bleached hair in the required amount. After an acting time of 30 minutes at 40° C. the hair is washed with a shampoo, rinsed with water and dried. The obtained color shades, color intensities and pH are summarized in Table III.

TABLE III

HAIR DYE PRECURSOR COMPOSITIONS CONTAINING
2-AMINOMETHYL-1,4-DIAMINOBENZENE TRIHYDROCHLORIDE

| Example | Coupler | pH Value | Color Shade | Intensity |
|---|---|---|---|---|
| 6a | 0.28 resorcinol | 10.0 | Medium blond | (++) |
| 6b | 0.27 g 3-aminophenol | 9.9 | Rosewood | (+) |
| 6c | 0.31 g 5-amino-2-methylphenol | 10.2 | Red-violet | (+) |
| 6d | 0.64 5-((2-hydroxy-ethyl)amino)-2-methoxyaniline dihydrochloride | 10.6 | Blue | (++) |

(o) = average, (+) = intense; (++) = very intense

Example 7

Oxidation Hair Dye Precursor Composition in Gel Form

| | |
|---|---|
| 15.25 g | oleic acid |
| 3.00 g | glycerol |
| 8.00 g | ethanol |
| 0.50 g | ascorbic acid |
| 0.40 g | sodium sulfite |
| 10.30 g | ammonia, 25% aqueous solution |
| 0.35 g | 2-aminomethyl-1,4-diaminobenzene disulfate |
| 0.21 g | 1,4-diamino-2-(2-hydroxyethyl)benzene sulfate |
| 0.50 g | 4,5-diamino-1-(2-hydroxyethyl)pyrazole sulfate |
| 0.31 g | 3-aminophenol |
| 0.13 g | resorcinol |
| 0.12 g | 2-chloro-6-(ethylamino)-4-nitrophenol |
| to 100.00 g | water, demineralized. |

Immediately prior to application 100 g of the above-described oxidation dye precursor composition is mixed with 100 grams of a 6% by weight aqueous hydrogen peroxide solution. The resulting ready-to-use hair dye mixture is applied to bleached hair in the required amount. After an acting time of 30 minutes at 40° C. the hair is washed with a shampoo, rinsed with water and dried. The dye hair color is red-brown with a high chromaticity and brightness.

Example 8

Hair Dye Solution with a Basic pH

| | |
|---|---|
| 10.00 g | ethanol |
| 10.00 g | sodium lauryl ether sulfate, 28% aqueous solution |
| 10.00 g | ammonia, 25% aqueous solution |
| 0.30 g | ascorbic acid |
| 0.75 g | 2-aminomethyl-1,4-diaminobenzene trihydrochloride |
| X g | coupler substance from Table IV |
| to 100.00 g | water, demineralized. |

Immediately prior to application 10 g of the above-described oxidation dye precursor-containing solution is mixed with 10 grams of a 6% by weight aqueous hydrogen peroxide solution. The resulting ready-to-apply hair dye mixture is applied to bleached hair in the required amount. After an acting time of 30 minutes at 40° C. the hair is washed with a shampoo, rinsed with water and dried. The obtained color shades, color intensities and pH are summarized in Table IV.

TABLE IV

HAIR DYE SOLUTIONS CONTAINING 2-AMINOMETHYL-1,4-DIAMINOBENZENE TRIHYDROCHLORIDE

| Example | Coupler | pH Value | Color Shade | Intensity |
|---|---|---|---|---|
| 8a | 0.60 g 1,3-diamino-4-(2-hydroxy-ethoxy)-benzene dihydrochloride | 10.7 | Blue | (+) |
| 8b | 0.39 g 3-amino-2-chloro-6-methylphenol | 10.5 | Violet | (+) |
| 8c | 0.45 g 3-amino-2,4-dichlorophenol | 10.6 | Aubergine | (+) |
| 8d | 0.56 2-chloro-5-((2,2,2-trifluoro-ethyl)amino)phenol | 10.7 | Blue | (+) |
| 8e | 0.61 3-amino-6-methoxy-2-methylamino)-pyridine dihydrochloride | 10.6 | Blue-green | (+) |
| 8f | 0.36 g 1-naphthol | 10.9 | Blue-violet | (+) |

(o) = average, (+) = intense; (++) = very intense

Example 9
Hair Dye Solution with a Basic pH

| | |
|---|---|
| 10.00 g | ethanol |
| 10.00 g | sodium lauryl ether sulfate, 28% aqueous solution |
| 10.00 g | ammonia, 25% aqueous solution |
| 0.30 g | ascorbic acid |
| 0.38 g | 2-aminomethyl-1,4-diaminobenzene trihydrochloride |
| X g | coupler substance from Table V |
| to 100.00 g | water, demineralized. |

Immediately prior to application 20 g of the above-described oxidation dye precursor-containing solution is mixed with 20 grams of a 6% by weight aqueous hydrogen peroxide solution. The resulting ready-to-use hair dye mixture is applied to bleached hair in the required amount. After an acting time of 30 minutes at 40° C. the hair is washed with a shampoo, rinsed with water and dried. The obtained color shades, color intensities and pH are summarized in Table V.

TABLE V

HAIR DYE SOLUTIONS CONTAINING 2-AMINOMETHYL-1,4-DIAMINOBENZENE TRIHYDROCHLORIDE

| Example | Coupler | pH Value | Color Shade | Intensity |
|---|---|---|---|---|
| 9a | 0.40 g 1,3-diamino-4-(2-hydroxy-ethoxy)-benzene dihydrochloride | 10.5 | Blue | (+) |
| 9b | 0.26 g 3-amino-2-chloro-6-methylphenol | 10.5 | Violet | (o) |
| 9c | 0.30 g 3-amino-2,4-dichlorophenol | 10.6 | Aubergine | (o) |
| 9d | 0.37 2-chloro-5-((2,2,2-trifluoro-ethyl)amino)phenol | 10.4 | Blue | (+) |
| 9e | 0.40 3-amino-6-methoxy-2-methylamino)-pyridine dihydrochloride | 10.4 | Blue-green | (o) |
| 9f | 0.24 g 1-naphthol | 10.5 | Blue-violet | (+) |

(o) = average, (+) = intense; (++) = very intense

Example 10
Dyeing Agent

A ready-to-apply cream mixture according to example 3 is applied to the textiles listed in Table VI. After an acting time of 30 minutes at 40° C., the cream mixture is neutralized and rinsed out with water.

TABLE VI

COLORS AND INTENSITIES OBTAINED BY DYEING VARIOUS TEXTILE FIBERS WITH EXEMPLARY COMPOSITIONS 3a, 3b, 3c and 3d

| Example | Textile Fibers | 3a | 3b | 3c | 3d |
|---|---|---|---|---|---|
| 10a | Cotton | medium brown (+) | bright brown (+) | rosé (o) | blue-gray (+) |
| 10b | Silk | medium brown (+) | brown (++) | rosé (++) | blue (+) |
| 10c | Wool | carmel (++) | dark brown (++) | red-violet (++) | blue-black (++) |
| 10d | Nylon 66 | medium blond (+) | bright brown (+) | red-brown (+) | aubergine (+) |

(o) average, (+) = intense; (++) = very intense

Unless otherwise indicated all percentages are percentages by weight.

The disclosure in German Patent Application 199 61 229.3 of Dec. 18, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in methods of making 2-aminomethyl-1,4-diaminobenzene and its physiologically compatible salts as well as compositions and methods for dyeing keratin fibers containing the 1,4-diamino-2-methoxymethyl-benzene and physiologically compatible salts thereof it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We claim:

1. A method of dyeing keratin fibers, said method comprising the steps of:

a) providing an oxidation dye precursor composition containing at least one coupler compound and at least one developer compound, said at least one developer compound including at least one member selected from the group consisting of 2-aminomethyl-1,4-diaminobenzene and physiologically compatible salts of said 2-aminomethyl-1,4-diaminobenzene; and b) mixing the oxidation dye precursor composition provided in step a) with an oxidizing agent to form a ready-to-apply dye mixture;

c) applying the ready-to-apply dye mixture to the keratin fibers to dye the keratin fibers.

2. The method as defined in claim 1, wherein said at least one developer compound includes at least one ingredient selected from the group consisting of p-phenylenediamine, substituted p-phenylenediamine compounds besides said 2-aminomethyl-1,4-diaminobenzene and said salts thereof, aminophenols, substituted aminophenols and substituted 4,5-diaminopyrazole compounds.

3. The method as defined in claim 1, wherein said oxidation dye precursor composition contains at least one direct-dyeing dye compound.

4. The method as defined in claim 1, wherein said keratin fibers are hairs.

5. The method as defined in claim 1 or 4, further comprising neutralizing the ready-to-apply dye mixture and allowing the ready-to-dye mixture to act on the keratin fibers at a temperature of from 15 to 50° C. for from 10 to 45 minutes.

6. A method of dyeing keratin fibers, said method comprising the steps of:

a) providing a dye-carrying composition comprising at least one member selected from the group consisting of oxidation dye precursor compounds and direct-dyeing dye compounds, said dye-carrying composition including at least one ingredient selected from the group consisting of 1,4-diamino-2-methoxy-methylbenzene and at least one physiologically compatible salt of said 2-aminomethyl-1,4-diaminobenzene; and b) applying the dye-carrying composition to the keratin fibers in order to dye the keratin fibers.

7. A ready-to-apply hair dye mixture made by a method comprising the steps of:

a) providing an oxidation dye precursor composition containing at least one coupler compound and at least one developer compound, said at least one developer compound including at least one member selected from the group consisting of 2-aminomethyl-1,4-diaminobenzene and physiologically compatible salts of said 2-aminomethyl-1,4-diaminobenzene; and b) mixing the oxidation dye precursor composition provided in step a) with an oxidizing agent immediately prior to application to form the ready-to-apply hair dye mixture.

8. The ready-to-apply hair dye mixture as defined in claim 7, wherein said at least one developer compound includes at least one ingredient selected from the group consisting of p-phenylenediamine, substituted p-phenylenediamine compounds besides said 2-aminomethyl-1,4-diaminobenzene and said salts thereof, eminophenois, substituted aminophenois and substituted 4,5-diaminopyrazole compounds.

9. The ready-to-apply hair dye mixture as defined in claim 7, wherein said at least one coupler compound and said at least one developer compound are present in a total amount of from 0.01 to 10 percent by weight.

10. The ready-to-apply hair dye mixture as defined in claim 7, wherein the oxidation dye precursor composition includes at least one direct-dyeing dye compound.

11. The ready-to-apply hair dye mixture as defined in claim 10, wherein the at least one direct-dyeing dye compound is present in a total amount of from 0.1 to 10 percent by weight.

12. The ready-to-apply hair dye mixture as defined in claim 7, wherein the oxidation dye precursor composition and the oxidizing agent are mixed with each other in a weight ratio of from 5:1 to 1:3 during the mixing.

13. The ready-to-apply hair dye mixture as defined in claim 7, having a pH of from 6 to 10.5.

* * * * *